United States Patent
Birchard

(10) Patent No.: US 8,192,399 B2
(45) Date of Patent: Jun. 5, 2012

(54) EXTENSION CONTROL HANDLE WITH ADJUSTABLE LOCKING MECHANISM

(75) Inventor: Christopher J. Birchard, Pasadena, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 844 days.

(21) Appl. No.: 12/125,890

(22) Filed: May 22, 2008

(65) Prior Publication Data

US 2009/0099513 A1    Apr. 16, 2009

Related U.S. Application Data

(60) Provisional application No. 60/939,649, filed on May 23, 2007.

(51) Int. Cl.
 *A61M 5/00* (2006.01)
(52) U.S. Cl. .................................. 604/117
(58) Field of Classification Search ............ 604/117
 See application file for complete search history.

(56) References Cited

U.S. PATENT DOCUMENTS

| | | | |
|---|---|---|---|
| 4,228,802 A | 10/1980 | Trott | |
| 4,391,199 A | 7/1983 | Morin | |
| 5,176,647 A | 1/1993 | Knoepfler | |
| 5,217,441 A * | 6/1993 | Shichman | 604/536 |
| 5,380,292 A * | 1/1995 | Wilson | 604/165.02 |
| 5,480,387 A * | 1/1996 | Gabriel et al. | 604/134 |
| 5,688,243 A * | 11/1997 | Rammler | 604/115 |
| 5,997,509 A * | 12/1999 | Rosengart et al. | 604/164.01 |
| 6,123,699 A | 9/2000 | Webster, Jr. | |
| 6,165,164 A | 12/2000 | Hill et al. | |
| 6,171,277 B1 | 1/2001 | Ponzi | |
| 6,183,463 B1 * | 2/2001 | Webster, Jr. | 604/528 |
| 6,201,387 B1 | 3/2001 | Govari | |
| 6,254,573 B1 | 7/2001 | Haim et al. | |
| 6,309,370 B1 | 10/2001 | Haim et al. | |
| 6,321,106 B1 | 11/2001 | Lemelson | |
| 6,385,472 B1 | 5/2002 | Hall et al. | |
| 6,484,118 B1 | 11/2002 | Govari | |

(Continued)

FOREIGN PATENT DOCUMENTS

EP    0 447 216 A1    9/1991

(Continued)

OTHER PUBLICATIONS

International Search Report, dated Aug. 27, 2008 for corresponding International Application No. PCT/US2008/064667, 4 sheets, indicating relevance of listed references on this IDS.
International Search Report for International Application No. PCT/US2008/064652, mailed Sep. 5, 2008, 7 pgs.
International Search Report for International Application No. PCT/US2008/064661, mailed Sep. 8, 2008, 6 pgs.

(Continued)

*Primary Examiner* — Jackie Ho
*Assistant Examiner* — Diva Ranade
(74) *Attorney, Agent, or Firm* — Christie, Parker & Hale, LLP

(57) ABSTRACT

The present invention is directed to a needle control handle which allows a needle extension distance to be adjusted, set and locked. In one embodiment, the control handle has an outer body and a piston adapted for relative longitudinal movement to extend the needle. A first control knob is movable on the piston for adjusting and setting the distance of the needle extension. A second knob is provided for releasably locking the first control knob on the piston once the needle extension distance has been set. Each of the knobs has a contact surface that enables the knobs to mutually lock with and release from each other.

17 Claims, 10 Drawing Sheets

U.S. PATENT DOCUMENTS

| | | | |
|---|---|---|---|
| 6,540,725 B1 * | 4/2003 | Ponzi | 604/272 |
| 6,575,931 B1 | 6/2003 | Ponzi | |
| 6,623,474 B1 | 9/2003 | Ponzi | |
| 6,980,843 B2 | 12/2005 | Eng et al. | |
| 7,399,294 B2 * | 7/2008 | Mickley | 604/117 |
| 2003/0117888 A1 | 6/2003 | Reilly et al. | |
| 2003/0195491 A1 | 10/2003 | Schneider et al. | |
| 2003/0233076 A1 | 12/2003 | Mickley et al. | |
| 2004/0039338 A1 | 2/2004 | Lee et al. | |
| 2004/0204672 A1 | 10/2004 | Palasis et al. | |
| 2009/0018497 A1 | 1/2009 | Birchard et al. | |
| 2009/0099514 A1 | 4/2009 | Birchard et al. | |

FOREIGN PATENT DOCUMENTS

| | | |
|---|---|---|
| WO | WO 99/59663 | 11/1999 |
| WO | WO 02/30554 A2 | 4/2002 |
| WO | WO 2004/014533 A1 | 2/2004 |
| WO | WO 2005/077441 A2 | 8/2005 |

OTHER PUBLICATIONS

International Search Report for International Application No. PCT/US2008/064667, mailed Sep. 9, 2008, 7 pgs.

* cited by examiner

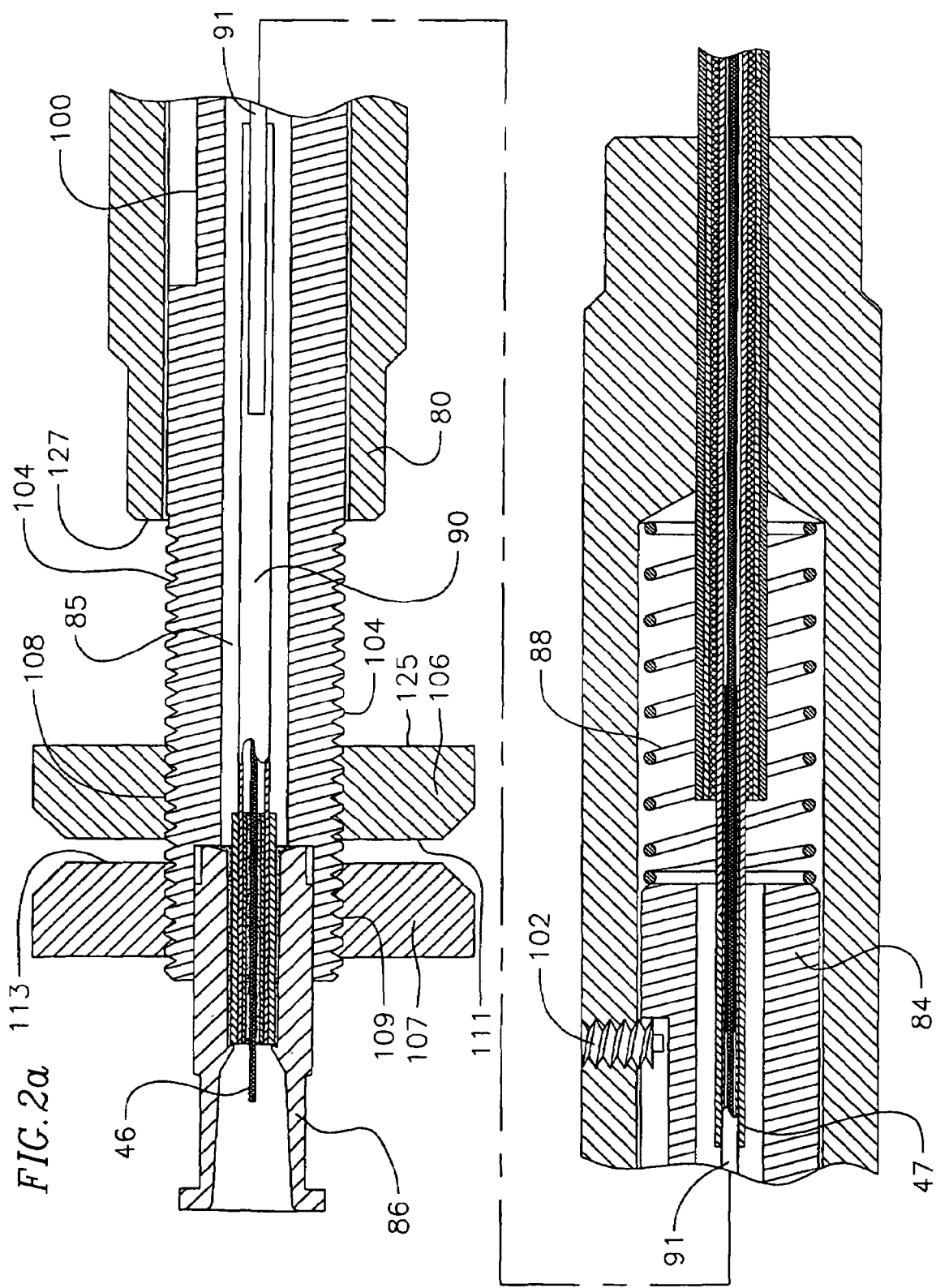

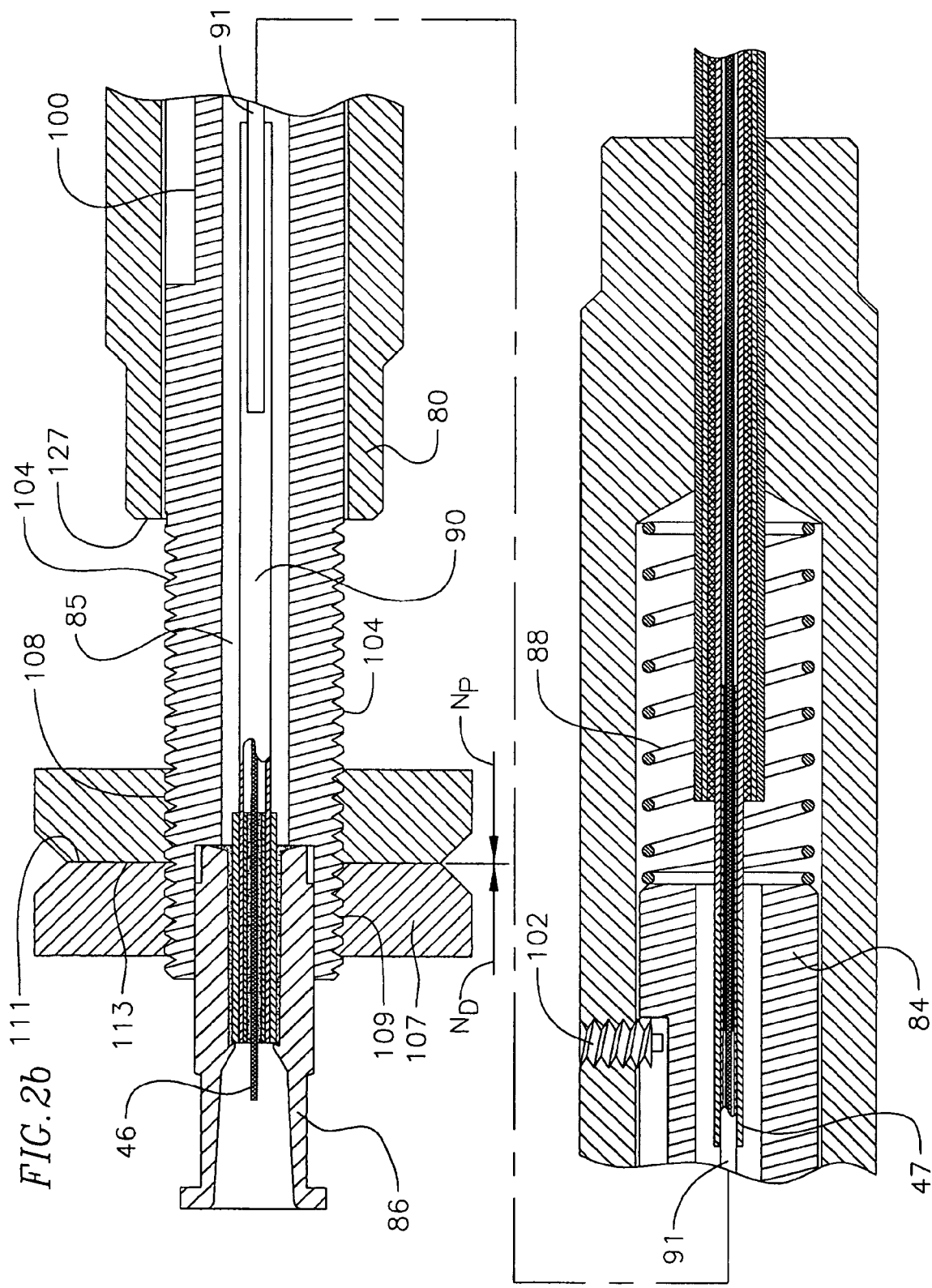

EXTENSION CONTROL HANDLE WITH ADJUSTABLE LOCKING MECHANISM

CROSS-REFERENCE TO RELATED APPLICATION(S)

This application claims priority to U.S. Provisional Application No. 60/939,649, filed May 23, 2007, the entire disclosure of which is hereby incorporated by reference.

FIELD OF INVENTION

This invention relates to a extension control handle for extending a component, including an injection needle, and more particularly to a catheter having a spring-loaded extension control handle for controlled extension of a component, including an injection needle.

BACKGROUND

Targeted delivery of therapeutic or diagnostic agents into heart tissue, such as the myocardium for revascularization treatment is very desirable. A potential benefit of targeted delivery is that there is an increased efficiency obtained by the precise placement of the therapeutic agent. For a percutaneous transluminal approach, injection catheters have been used successfully as they can overcome problems such as obtaining access to the delivery site and transporting the therapeutic agent to the desired site. Success has also stemmed from the ability of the physician to steer the distal end of the catheter to a desired location, position the distal tip of the catheter at precisely the same location where prior measurements have indicated that the drug should be infused, extending the injection needle to a proper depth within the myocardium, and retract to enable safe repositioning and removal of the catheter.

Needle control handles are known for use in controlling extension and retraction of catheter injection needles. For example, U.S. Pat. Nos. 6,540,725 and 6,623,474, the entire disclosures of which are hereby incorporated by reference, are directed to injection catheters with needle control handles having a piston arrangement for extending and retracting the injection needle. While an adjustable thumb control allows a user to adjust the throw of the piston (which in turn adjusts the distance by which the needle can extend), a separate tool is necessary to adjust the tension of the thumb control and/or to lock the thumb control in place. To provide a tool with each catheter would be undesirable for multiple reasons, including an increase in the overall cost of the catheter and the need to sterilize the tool. Accordingly, it is desirable to provide a needle control handle whose thumb control can be readily adjusted and releasably locked in a predetermined position. It is also desirable to provide a catheter having a control handle for actuating longitudinal movement of a component relative to at least the catheter body whereby the thumb control setting the amount of the longitudinal movement can be adjusted and readily locked in a predetermined position.

SUMMARY OF THE INVENTION

The present invention is directed to a needle control handle which allows a needle extension distance to be adjusted, set and locked. In one embodiment, the control handle has an outer body and a piston adapted for relative longitudinal movement to extend the needle. A first control knob is movable on the piston for adjusting and setting the distance of the needle extension. A second knob is provided for releasably locking the first control knob on the piston once the needle extension distance has been set. The knobs have friction-inducing surfaces that enable a mutually releasable locking engagement.

In a more detailed embodiment, the handle includes an injection needle, an outer body and a piston adapted for longitudinal movement relative to the outer body. First and second controls are movably mounted on the piston such that the position of the first control limits the longitudinal movement of the piston and the needle relative to the outer body, and the second control is adapted to releasably lock the first control at a set position on the piston. A longitudinal force applied to at least one of the controls causes longitudinal movement of the piston and the needle relative to outer body.

In another embodiment includes a catheter and a needle control handle having an outer body having a piston chamber and a piston slidably mounted within the piston chamber, such longitudinal force applied to one of the outer body and the piston causes longitudinal movement of the injection needle to extend past the distal end of the catheter. An adjustable thumb control mounted on the piston control limits the longitudinal movement of the piston relative to the outer body. A locking thumb control releasably engages with the thumb control to lock the latter in a predetermined position.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 2a is a side cross-sectional view of the needle control handle where the needle is in a retracted position and a thumb control is unlocked.

FIG. 2b is a side cross-sectional view of the needle control handle where the needle is in a retracted position and a thumb control is locked with a locking thumb control.

DETAILED DESCRIPTION OF THE INVENTION

Figure 1:
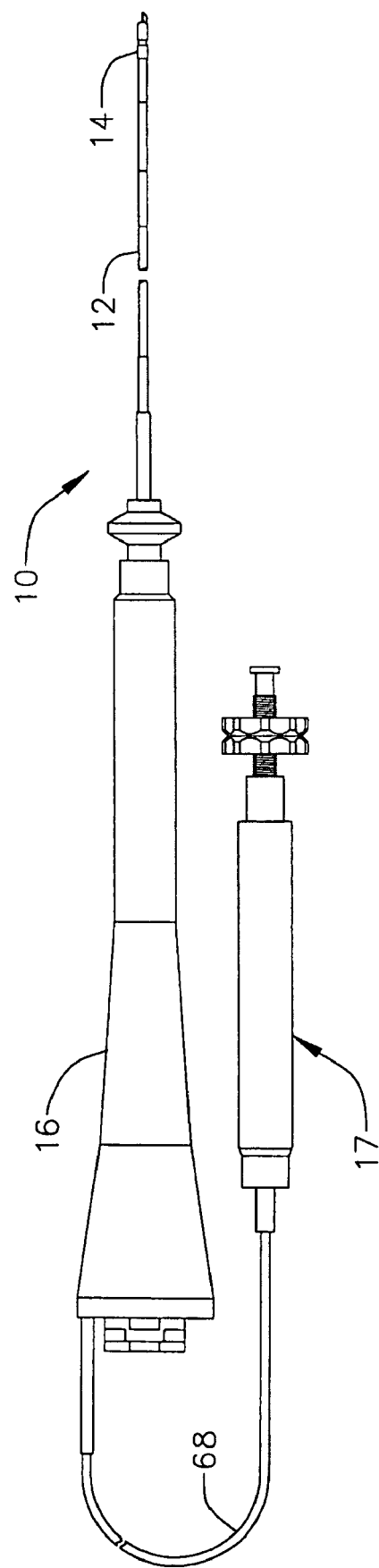
FIG. 1 is a side plan view of one embodiment of the catheter of the present invention.

In a disclosed embodiment of the invention, there is provided a catheter for use for injection of a therapeutic or diagnostic agent into the heart. As shown in FIG. 1, catheter 10 comprises an elongated catheter body 12 having proximal and distal ends, a tip section 14 at the distal end of the catheter body 12, a deflection control handle 16 at the proximal end of the catheter body 12, and a needle control handle 17 attached indirectly to the catheter body proximal the deflection control handle.

Figure 5:
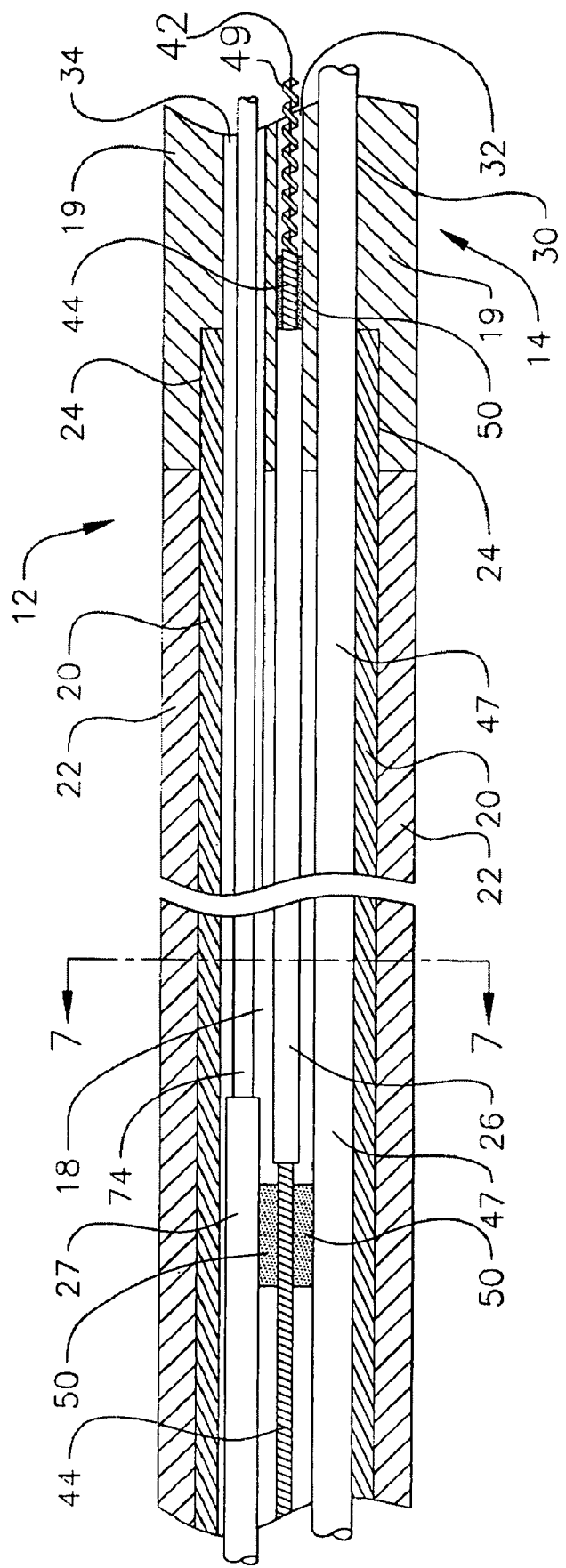
FIG. 5 is a side cross-sectional view of the catheter body, including the junction between the catheter body and the catheter tip section.
Figure 7:
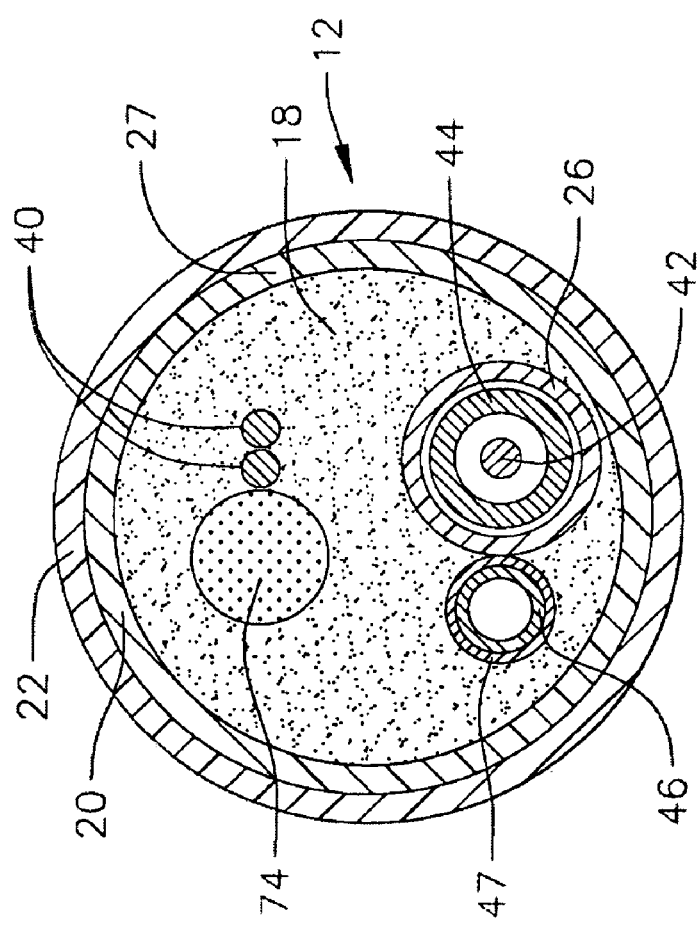
FIG. 7 is a transverse cross-sectional view of the catheter body along line 7-7; and, FIG. 8 is a side cross-sectional view of the catheter handle.

With reference to FIGS. 5 and 7, the catheter body 12 comprises a single, central or axial lumen 18. The catheter body 12 is flexible, i.e., bendable, but substantially non-compressible along its length. The catheter body 12 may be of any suitable construction and made of any suitable material. A presently preferred construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, preferably polyimide. The stiffening tube, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is presently preferred because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used.

A particularly preferred catheter has an outer wall 22 with an outer diameter of about 0.092 inch and an inner diameter of about 0.063 inch and a polyimide stiffening tube having an outer diameter of about 0.0615 inch and an inner diameter of about 0.052 inch.

Figure 3:
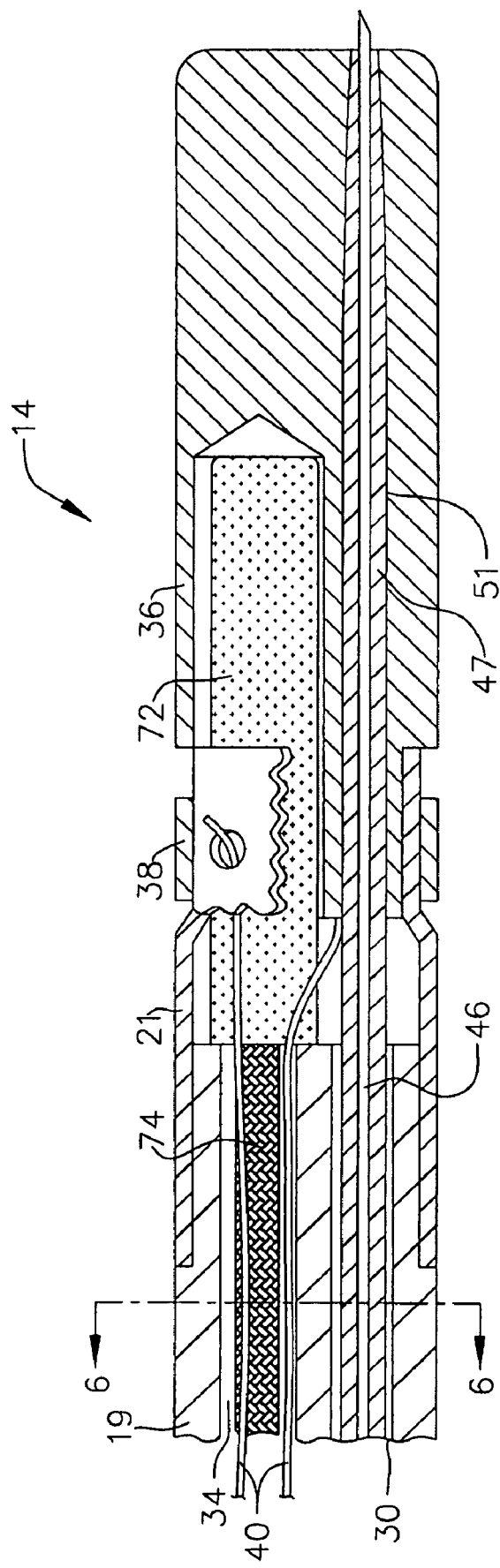
FIG. 3 is a side cross-sectional view of the catheter section showing an embodiment having three lumens and showing the position of the electromagnetic mapping sensor and the injection needle.
Figure 4:
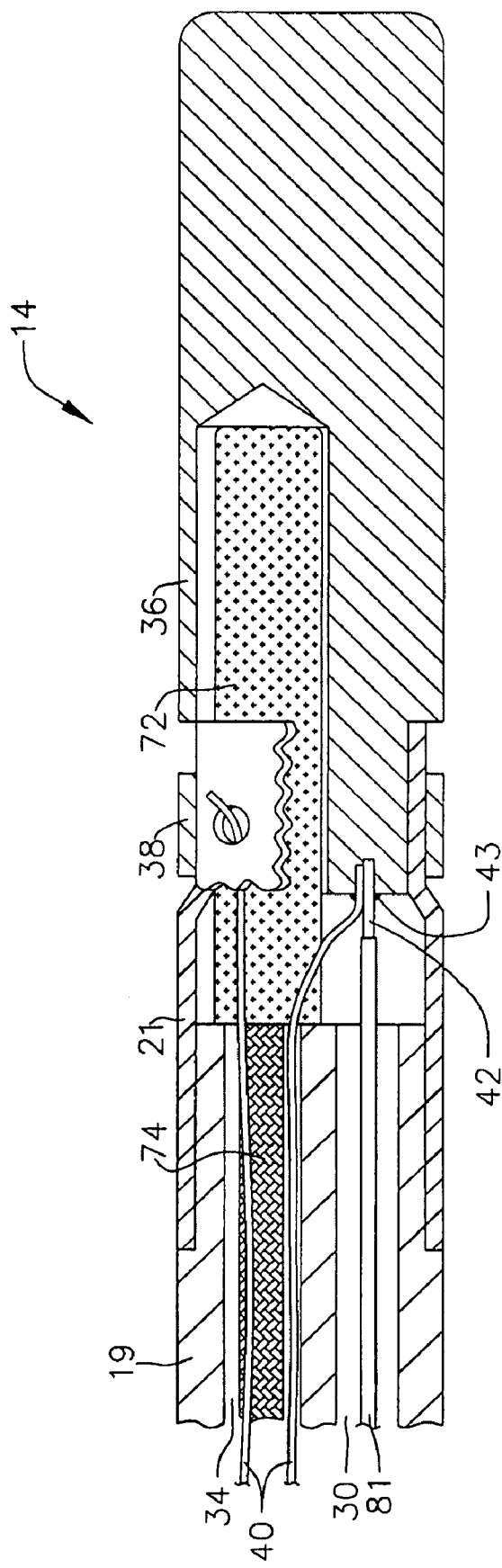
FIG. 4 is a side cross-sectional view of the catheter tip section showing an embodiment having three lumens and showing the position of the electromagnetic mapping sensor and the puller wire.
Figure 6:
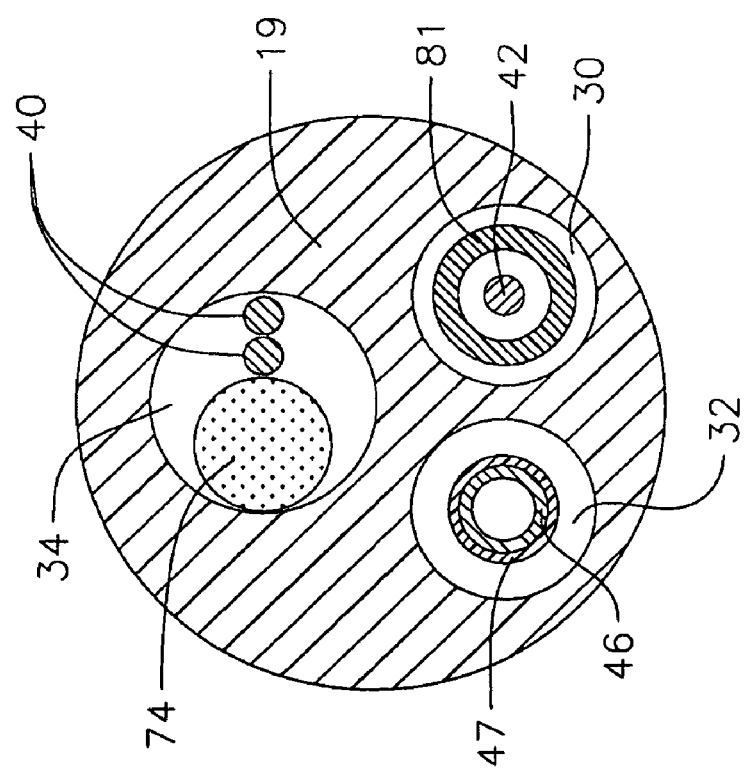
FIG. 6 is a transverse cross-sectional view of the catheter tip section along line 6-6 showing an embodiment having three lumens.

As shown in FIGS. 3, 4 and 6, the tip section 14 comprises a short section of tubing 19 having three lumens 30, 32 and 34. The tubing 19 is made of a suitable non-toxic material which is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 8 French. The size of the lumens is not critical. In a particularly preferred embodiment, the tip section has an outer diameter of about 7 French (0.092 inch) and the first lumen 30 and second lumen 32 are generally about the same size, having a diameter of about 0.022 inch, with the third lumen 34 having a slightly larger diameter of about 0.036 inch.

A means for attaching the catheter body 12 to the tip section 14 is illustrated in FIG. 5. The proximal end of the tip section 14 comprises an inner counter bore 24 that receives the outer surface of the polyimide stiffener 20. The tip section 14 and catheter body 12 are attached by glue or the like.

The stiffening tube 20 is held in place relative to the outer wall 22 at the proximal end of the catheter body 12. In preferred construction of the catheter body 12, a force is applied to the proximal end of the stiffening tube 20 which causes the distal end of the stiffening tube 20 to firmly push against the counter bore 24. While under compression, a first glue joint is made between the stiffening tube 20 and the outer wall 22 by a fast drying glue, e.g. Super Glue®. Thereafter a second glue joint is formed between the proximal ends of the stiffening tube 20 and outer wall 22 using a slower drying but stronger glue, e.g., polyurethane.

As shown in FIG. 7, extending through the single lumen 18 of the catheter body 12 are lead wires 40, an injection needle 46, a sensor cable 74, and a compression coil 44 through which a puller wire 42 extends. A single lumen 18 catheter body is preferred over a multi-lumen body because it has been found that the single lumen 18 body permits better tip control when rotating the catheter 10. The single lumen 18 permits the lead wires 40, the injection needle 46, the sensor cable 74, and the puller wire 42 surrounded by the compression coil 44 to float freely within the catheter body. If such wires and cables were restricted within multiple lumens, they tend to build up energy when the handle 16 is rotated, resulting in the catheter body 12 having a tendency to rotate back if, for example, the handle is released, or if bent around a curve, to flip over, either for which are undesirable performance characteristics.

With reference to FIGS. 3 and 4, mounted at the distal end of the tip section 14 is a tip electrode 36. Preferably the tip electrode 36 has a diameter about the same as the outer diameter of the tubing 19. The tip electrode 36 is connected to the tubing 19 by means of a plastic housing 21, preferably made of polyetheretherketone (PEEK). The proximal end of the tip electrode 36 is notched circumferentially and fits inside the distal end of the plastic housing 21 and is bonded to the housing 21 by polyurethane glue or the like. The proximal end of the plastic housing 21 is bonded with polyurethane glue or the like to the distal end of the tubing 19 of the tip section 14. Alternatively, the tip electrode 36 can be mounted directly to the distal end of the flexible tubing 19 of the tip section 14.

Mounted on the distal end of the plastic housing 21 is a ring electrode 38. The ring electrode 38 is slid over the plastic housing 21 and fixed in place by glue or the like. If desired, additional ring electrodes may be used and can be positioned over the plastic housing 21 or over the flexible tubing 19 of the tip section 14.

The tip electrode 36 and ring electrode 38 are each connected to separate lead wires 40. The lead wires 40 extend through the third lumen 34 of tip section 14, the catheter body 12, and the control handle 16, and terminate at their proximal end in an input act (not shown) that may be plugged into an appropriate monitor (not shown). If desired, the portion of the lead wires 40 extending through the catheter body 12, control handle 16 and proximal end of the tip section 14 may be enclosed or bundled within a protective tube or sheath.

The lead wires 40 are attached to the tip electrode 36 and ring electrode 38 by any conventional technique. Connection of lead wire 40 to the tip electrode 36 is preferably accomplished by weld 43, as shown in FIG. 4.

A puller wire 42 is provided for deflection of the tip section 14. The puller wire 42 is anchored at its proximal end to the control handle 16 and anchored at its distal end to the tip section 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches. It is understood that the present invention may also incorporate a magnetically-guided catheter, such as those disclosed in U.S. Pat. Nos. 6,385,472 and 6,980,843 and co-pending application entitled Magnetically Guided Catheter with Concentric Needle Port, naming inventors Christopher J. Birchard, et al., application Ser. No. 12/125,903, filed on even date herewith.

The compression coil 44 extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. For example, when the puller wire 42 has a diameter of about 0.007 inches, the compression coil 44 preferably has an inner diameter of about 0.008 inches. The Teflon® coating on the puller wire 42 allows it to slide freely within the compression coil 44. Along its length, the outer surface of the compression coil 44 is covered by a flexible, non-conductive sheath 26 to prevent contact between the compression coil 44 and any of the lead wires 40, injection needle 46 or sensor cable 74. A non-conductive sheath 26 made of polyimide tubing is presently preferred.

As shown in FIGS. 4 and 5, the compression coil 44 is anchored at its proximal end to the proximal end of the stiffening tube 20 in the catheter body 12 by glue to form a glue joint 50 and at its distal end to the tip section 14 in the second lumen 32. The glue may be applied by means of a syringe or the like through a hole made between the outer surface of the catheter body 12 and the single lumen.

The puller wire 42 extends into the second lumen 32 of the tip section 14. The distal end of the puller wire 42 is anchored to the tip electrode 36 or to the side of the catheter tip section 14. With reference to FIGS. 4 and 5, within the tip section 14, and distal to the glue joint 50, the turns of the compression coil are expanded longitudinally. Such expanded turns 49 are both bendable and compressible and preferably extend for a length of about 0.5 inch. The puller wire 42 extends through the expanded turns 49 then into a plastic, preferably Teflon®, sheath 81, which prevents the puller 42 from cutting into the wall of the tip section 14 when the section 14 is deflected.

An injection needle 46 is provided, which extends from the needle control handle through the catheter body 12, through the first lumen 30 of the tip section 14 and through a passage 51 in the tip electrode 36. The injection needle 46 is formed of Nitinol, and, as illustrated in FIG. 3, is preferably formed with a beveled edge at the distal tip of the needle. The needle 46 is coaxially mounted within a protective tube 47, preferably made of polyimide, which serves to prevent the needle from buckling and also serves to electrically insulate the needle from the distal electrode 36. The protective tube 47 additionally serves to provide a fluid-tight seal surrounding the injection needle 46. FIG. 3 depicts the injection needle 46 extending beyond the distal end of the tip electrode 36, as it would be positioned in order to infuse diagnostic or therapeutic fluid into the human heart. The distal end of the injection needle 46 is withdrawn into the tip electrode 36 during the period of time that the catheter is inserted through the vasculature of the body and also during the period of time in which the catheter is removed from the body to avoid injury. Alternatively, the tip section 14 can be provided without a tip electrode 36, in which case the distal end of the injection needle 46 could be retracted into the first lumen 30 of the tip section 14.

Additionally, an electromagnetic sensor 72 is contained within the distal end of the tip section 14. The electromagnetic sensor 72 is connected to an electromagnetic sensor cable 74, which extends through the third lumen 34 of the tip section 14 through the catheter body 12 into the control handle 16. The electromagnetic sensor cable 74 comprises multiple wires encased within a plastic sheath. In the control handle 16, the wires of the sensor-cable 74 are connected to a circuit board 64. The circuit board 64 amplifies the signal received from the electromagnetic sensor and transmits it to a computer in a form understandable by the computer. Also, because the catheter is designed for single use only, the circuit board contains an EPROM chip which shuts down the circuit board after the catheter has been used. This prevents the catheter, or at least the electromagnetic sensor, from being used twice. A suitable electromagnetic sensor is described, for example, in U.S. Pat. No. 4,391,199, which is hereby incorporated by reference. A preferred electromagnetic mapping sensor 72 is manufactured by Biosense Ltd. Israel and marketed under the trade designation NOGA. To use the electromagnetic sensor 72, the patient is placed in a magnetic field generated, for example, by situating under the patient a pad containing coils for generating a magnetic field. A reference electromagnetic sensor is fixed relative to the patient, e.g., taped to the patient's back, and the injection catheter containing a second electromagnetic sensor is advanced into the patient's heart. Each sensor comprises three small coils which in the magnetic field generate weak electrical signals indicative of their position in the magnetic field. Signals generated by both the fixed reference sensor and the second sensor in the heart are amplified and transmitted to a computer which analyzes the signals and then displays the signals on a monitor. By this method, the precise location of the sensor in the catheter relative to the reference sensor can be ascertained and visually displayed. The sensor can also detect displacement of the catheter that is caused by contraction of the heart muscle.

Using this technology, the physician can visually map a heart chamber. This mapping is done by advancing the catheter tip into a heart chamber until contact is made with the heart wall. This position is recorded and saved. The catheter tip is then moved to another position in contact with the heart wall and again the position is recorded and saved.

The electromagnetic mapping sensor 72 can be used alone or more preferably in combination with the tip electrode 36 and ring electrode 38. By combining the electromagnetic sensor 72 and electrodes 36 and 38, a physician can simultaneously map the contours or shape of the heart chamber, the electrical activity of the heart, and the extent of displacement of the catheter and hence identify the presence and location of the ischemic tissue. Specifically, the electromagnetic mapping sensor 72 is used to monitor the precise location of the tip electrode in the heart and the extent of catheter displacement. The tip electrode 36 and ring electrode 38 are used to monitor the strength of the electrical signals at that location. Healthy heart tissue is identified by strong electrical signals in combination with strong displacement. Dead or diseased heart tissue is identified by weak electrical signals in combination with dysfunctional displacement, i.e., displacement in a direction opposite that of healthy tissue. Ischemic, or hibernating or stunned, heart tissue is identified by strong electrical signals in combination with impaired displacement. Hence, the combination of the electromagnetic mapping sensor 72 and tip and ring electrodes 36 and 38 is used as a diagnostic catheter to determine whether and where to infuse a drug into the wall of the heart. Once the presence and location of ischemic tissue has been identified, the tip section 14 of the catheter can be deflected so that the injection needle 46 is generally normal, i.e., at a right angle, to the ischemic tissue, and the injection needle may then be extended out of the distal end of the tip electrode 36 and into the wall of the heart.

It is understood that, while it is preferred to include both electrophysiology electrodes and an electromagnetic sensor in the catheter tip, it is not necessary to include both. For example, an injection catheter having an electromagnetic sensor but no electrophysiology electrodes may be used in combination with a separate mapping catheter system. A preferred mapping system includes a catheter comprising multiple electrodes and an electromagnetic sensor, such as the NOGA-STAR catheter marketed by Biosense Webster, Inc., and means for monitoring and displaying the signals received from the electrodes and electromagnetic sensor, such as the Biosense-NOGA system, also marketed by Biosense Webster, Inc.

The electrode lead wires 40 and electromagnetic sensor cable 74 must be allowed some longitudinal movement within the catheter body so that they do not break when the tip section 14 is deflected. As shown in FIG. 5, to provide for such lengthwise movement, there is provided a tunnel through the glue joint 50, which fixes the proximal end of the compression coil 44 inside the catheter body 12. The tunnel is formed by a transfer tube 27, preferably made of a short segment of polyimide tubing. The transfer tube is approximately 60 mm long and has an outer diameter of about 0.021 inch and an inner diameter of about 0.019 inch.

Figure 8:
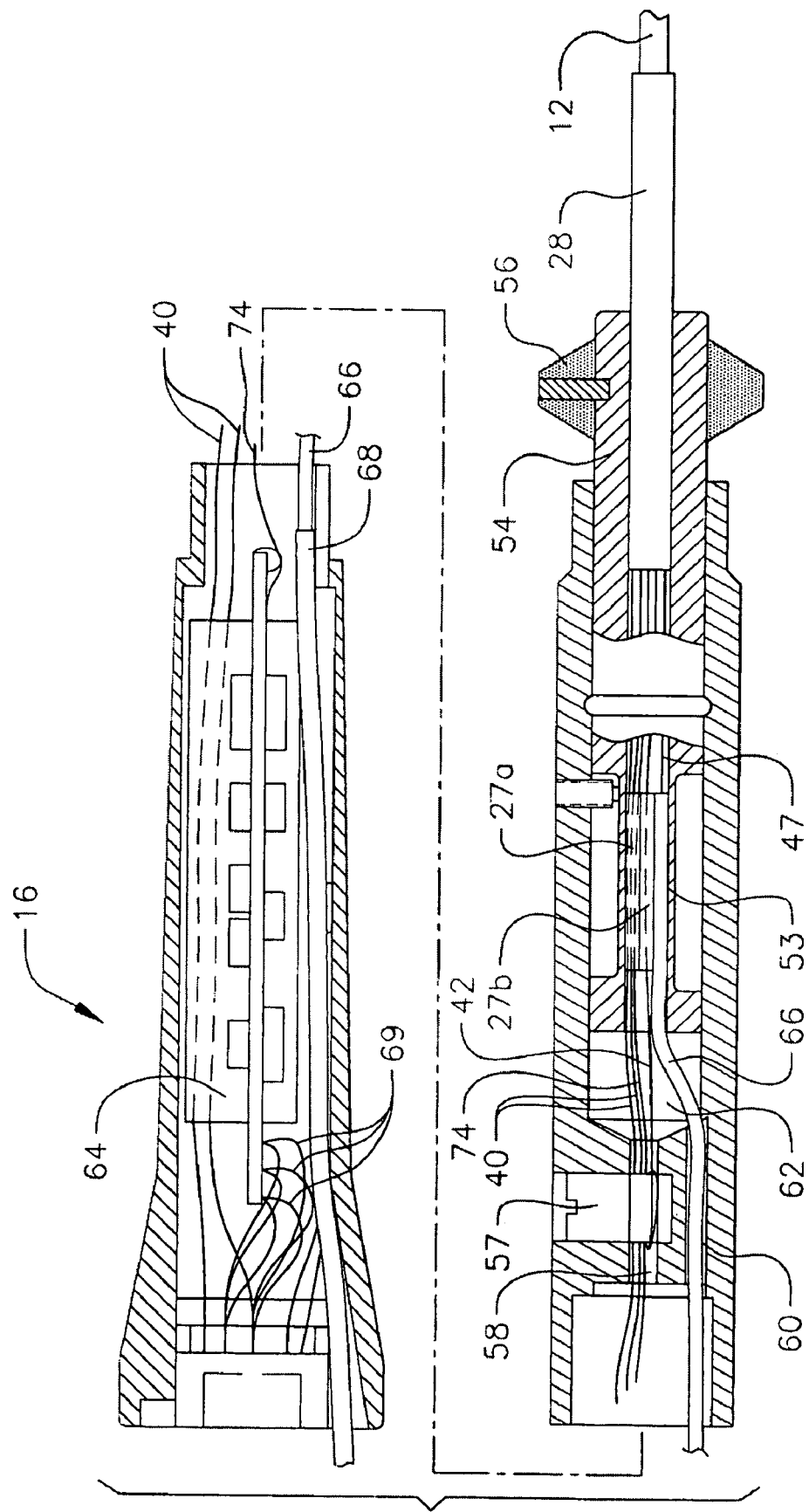

Longitudinal movement of the puller wire 42 relative to the catheter body 12, which results in deflection of the tip section 14, is accomplished by suitable manipulation of the control handle 16. As shown in FIG. 8, the distal end of the control handle 16 comprises a piston 54 with a thumb control 56 for manipulating the puller wire 42. The proximal end of the catheter body 12 is connected to the piston 54 by means of a shrink sleeve 28.

The injection needle 46 within the protective tube 47, the puller wire 42, the lead wires 40 and the electromagnetic sensor cable 74 extend through the piston 54. The puller wire 42 is anchored to an anchor pin 57 located proximal to the piston 54. The lead wires 40 and electromagnetic sensor cable 74 extend through a first tunnel 58, located near the side of the control handle 16. The electromagnetic sensor cable 74 connects to the circuit board 64 in the proximal end of the control handle. Wires 69 connect the circuit board 64 to a computer and imaging monitor (not shown).

The injection needle 46 and protective tube 47 extend through a guide tube 66, preferably made of polyurethane, and are afforded longitudinal movement therein. The guide tube 66 is anchored to the piston 54, preferably by glue at glue joint 53. This design allows the needle 46 and protective tube 47 longitudinal movement within the control handle 16 so that the needle 46 does not break when the piston 54 is adjusted to manipulate the puller wire 42. Within the piston 54, the puller wire 42 is situated within a transfer tube 27a, and the electromagnetic sensor cable 74 and lead wires 40 are situated within another transfer tube 27b to allow longitudinal movement of the wires and cable near the glue joint 53.

The injection needle 46, protective tube 47 and guide tube 66 extend through a second tunnel 60 situated near the side of the control handle 16 opposite the anchor pin 57. To avoid undesirable bending of the injection needle 46, a space 62 is provided between the proximal end of the piston 54 and the distal end of the second tunnel 60. Preferably the space 62 has a length of at least 0.50 inch and more preferably about from about 0.60 inch to about 0.90 inch.

In the proximal end of the control handle 16, the injection needle 46, protective tube 47 and polyurethane guide tube 66 extend through a second larger plastic guide tube 68, preferably made of Teflon®, which affords the guide tube 66, injection needle 46, and protective tube 47 longitudinal slidable movement. The second guide tube 68 is anchored to the inside of the control handle 16 by glue or the like and extends proximally beyond the control handle 16. The second guide tube 68 protects the injection needle 46 both from contact with the circuit board 64 and from any sharp bends as the guide tube 66, needle 46, and protective tube 47 emerge from the control handle 16.

Figure 2C:
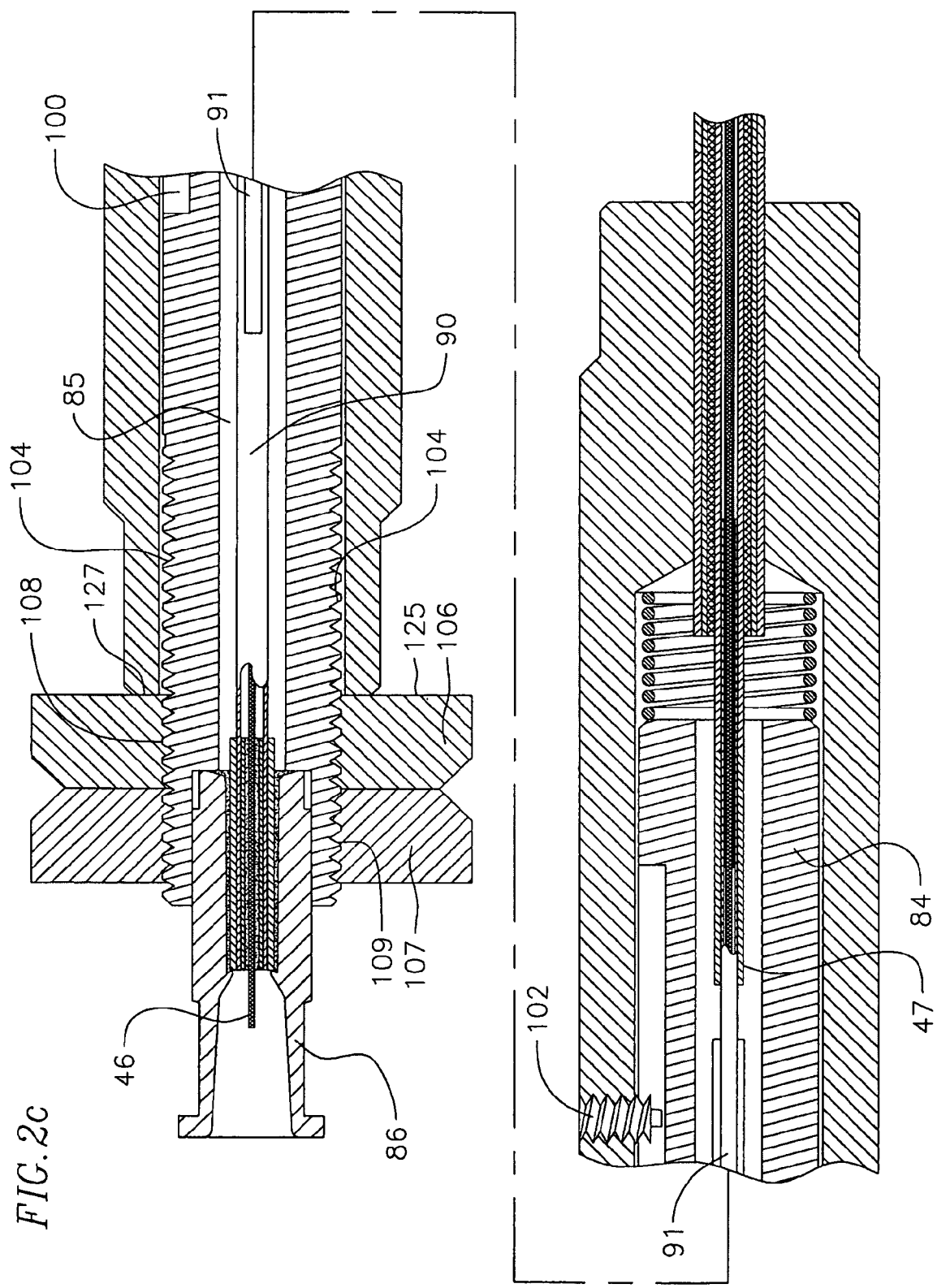
FIG. 2c is a side cross-sectional view of the needle control handle where the needle is in an extended position and a thumb control is locked with a locking thumb control.

Extension and retraction of the injection needle 46 out the distal end of the tip electrode 36 is accomplished by the needle control handle 17. As illustrated in FIGS. 2a, 2b and 2c, in one embodiment, the needle control handle 17 comprises a generally cylindrical outer body 80 having proximal and distal ends, a piston chamber 82 extending a part of the way therethrough, and a needle passage 83 extending a part of the way therethrough. The piston chamber 82 extends from the proximal end of the handle part way into the body 80, but does not extend out the distal end of the body. The needle passage 83, which has a diameter less than that of the piston chamber 82, extends from the proximal end of the piston chamber to the proximal end of the outer body 80.

A piston 84, having proximal and distal ends, is slidably mounted within the piston chamber 82. A Luer connector 86 is mounted in the distal end of the outer body. The piston 84 has an axial passage 85 through which the injection needle 46 extends, as described in more detail below. A compression spring 88 is mounted within the piston chamber 82 between the distal end of the piston 84 and the outer body 80. The compression spring 88 can either be arranged between the piston 84 and outer body 80, or can have one end in contact with or fixed to the piston 84, while the other end is in contact with or fixed to the outer body 80.

The proximal end of the injection needle 46 is mounted either directly or indirectly to the Luer connector 86 by means of a first rigid tube 90, preferably made of stainless steel, which has a proximal end fitted into the Luer connector. This arrangement fixedly attaches the injection needle 46 to the piston 84 so that it moves longitudinally with the piston. The first rigid tube 90 is also fixedly attached either directly or indirectly to the piston 84 and moves longitudinally with the piston. In the embodiment illustrated in FIGS. 2a and 2b, the first rigid tube 90 is attached to the proximal end of the piston 84, alternatively the first rigid tube 90 can be attached anywhere along the length of the piston 84. The injection needle 46 and first rigid tube 90 extend through the axial passage 85 of the piston 84. Within the axial passage 85, a second rigid tube 91, preferably made of stainless steel, has a proximal end mounted coaxially within or surrounding the distal end of the first rigid tube 90. The proximal end of the second rigid tube 91 is mounted within the protective tube 47, which has its proximal end inside the axial passage 85, and the distal end of the second rigid tube is attached, directly or indirectly, to the outer body 80. The second guide tube 68 containing the guide tube 66, through which the protective tube 47 and injection needle 46 extend, as discussed above, is fixedly attached to the outer body 80 by means of a shrink sleeve 92, as is generally known in the art.

In use, force is applied to the piston 84 to cause distal movement of the piston relative to the outer body 80, which compresses the compression spring 88. This movement causes the injection needle 46 to correspondingly move distally relative to the outer body, guide tube 66, protective tube 47 and catheter body 12, so that the distal end of the injection needle extends outside the distal end of the tip electrode 36. When the force is removed from the piston, the compression spring 88 pushes the piston 84 proximally to its original position, thus causing the distal end of the injection needle 46 to retract back into the tip electrode 36. Upon distal movement of the piston 84, the first rigid tube 90 moves distally over the second rigid tube 91 to prevent the injection needle 46 from buckling within the axial passage 85.

The piston 84 further comprises a longitudinal slot 100 extending along a portion of its outer edge. A securing means, such as a set screw, pin, or other locking mechanism 102 extends through the outer body 80 and into the longitudinal slot 100. This design limits the distance that the piston can be slid proximally out of the piston chamber 82. When the distal end of the injection needle 46 is in the retracted position, preferably the securing means 102 is at or near the distal end of the longitudinal slot 100.

The proximal end of the piston 84 has a threaded outer surface 104. A circular thumb control 106 is rotatably mounted on the proximal end of the piston. The thumb control 106 has a threaded inner surface 108 that interacts with the threaded outer surface 104 of the piston. The thumb control 106 acts as a stop, limiting the distance that the piston 84 can be pushed into the piston chamber 82, and thus the distance that the injection needle 46 can be extended out the distal end of the catheter. The threaded surfaces of the thumb control 106 and piston 84 allow the thumb control to be moved closer or farther from the proximal end of the outer body 80 so that the extension distance of the injection needle can be controlled by the physician.

A locking thumb control 107 is rotatably mounted on the piston proximal of and opposing the thumb control 106. The locking thumb control 107 also has a threaded inner surface 109 that interacts with the threaded outer surface 104 of the piston. The locking thumb control 106 functions to releasably lock the thumb control 106 in a predetermined position on the piston 84 so that the latter cannot inadvertently move from the position thereby changing the distance that the injection needle 46 can be extended out the distal end of the catheter.

Figure 2G:
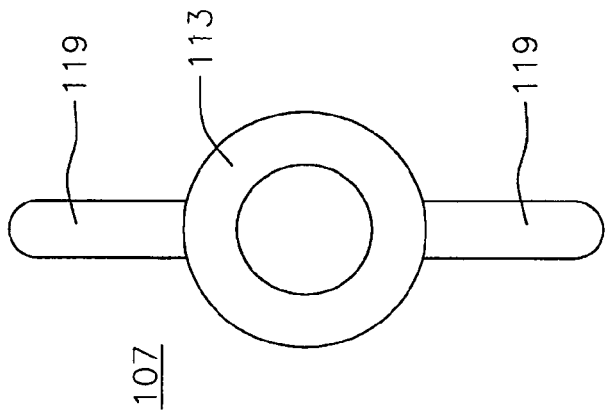
FIG. 2g is a front view of the locking thumb control of FIG. 2f.
Figure 2E:
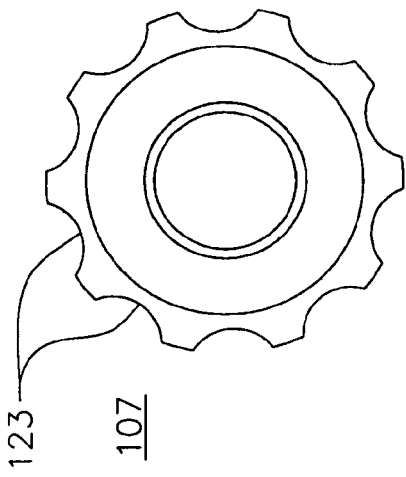
FIG. 2e is a front view of the locking thumb control of FIG. 2d.
Figure 2F:
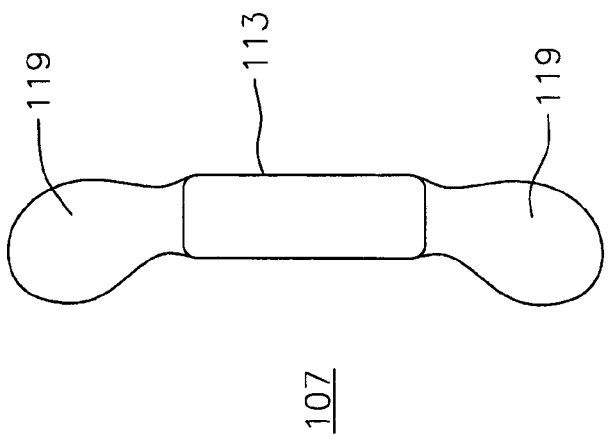
FIG. 2f is a side view of another embodiment of a locking thumb control.
Figure 2D:
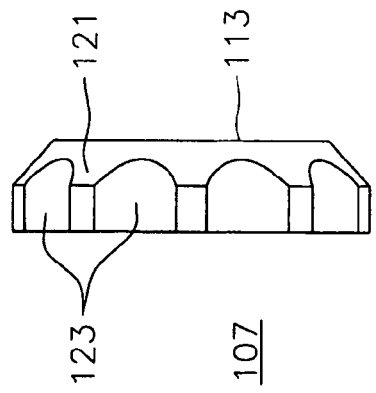
FIG. 2d is a side view of one embodiment of a locking thumb control.

In the illustrated embodiments of FIGS. 2d-2e, both controls 106 and 107 are circular knobs 121 contoured with friction-inducing formations 123 to facilitate handling and rotation by the user. In the disclosed embodiment of FIGS. 2a-2c, the controls 106 and 107 are oriented as mirror images of each other in an opposing configuration with the respective formations 123 of each control facing away from each other.

In use, the physician or user rotates the locking control 107 to move it proximally from the thumb control 106 so as to maximize the possible range of positions the thumb control 106 can occupy on the threaded portion of the piston 84. He then rotates the thumb control 106 to move it on the piston so as to set the "throw" or distance of extension of the injection needle beyond the distal end of the tip section (FIG. 2a). The more distance there is between a distal surface 125 of the thumb control 106 and the proximal end 127 of the outer body 80, the greater the "throw" of the injection needle, and vice versa. After the position of the thumb control 106 is determined (and the throw is set), the thumb control 106 is held in place on the piston 84 by one hand of the user while the locking thumb control 107 is turned by the other hand toward the thumb control 106. As proximal surface 111 of the thumb control 106 and distal surface 113 of the locking thumb control 107 contact each other, the user continues to turn the locking thumb control 107 until further rotation is difficult to achieve, at which occurrence the two controls mutually "lock" with each other (FIG. 2b). While in this locking contact engagement, neither controls can be readily rotated due to the normal forces N exerted by each surface 111 and 113 onto the other in opposing directions along the longitudinal axis of the handle 17 which cause the threaded surface of the controls to frictionally engage the threaded surface of the piston 84. In particular, the normal force $N_D$ exerted by the locking thumb control 107 on the thumb control 106 in the distal direction causes all distally-facing threaded surfaces of the thumb control 106 to frictionally engage contacting proximally facing threaded surfaces of the piston 84, while the normal force $N_P$ exerted by the thumb control 106 on the locking thumb control 107 in the proximal direction causes all proximally facing threaded surfaces of the locking thumb control 107 to frictionally engage contacting distally facing threaded surfaces of the piston 84. With the controls 106 and 107 in such mutually locking engagement, the user can apply a force distally onto the locking thumb control 107 and/or the thumb control 106 to actuate the piston to extend the needle (FIG. 2c) with the assurance that the locked predetermined position of the control 106 (and hence the throw the injection needle) has not changed. It is intended that the longitudinal force is sufficient to establish contact between the distal surface 125 of the control 106 and the proximal end 127 of the outer body 80. The controls 106 and 107 remain in mutual locking engagement throughout injection cycle(s) of needle extension, delivery of injectacte and needle retraction, until either or both of the controls 106 and 107 are rotated in opposite directions to separate, at which occurrence the needle extension can be set to a new distance by readjusting the position of the thumb control 106 and locking it in place in the new position with the locking control 107.

As would be recognized by one skilled in the art, the controls 106 and 107 need not mirror the size, shape or configuration of each other. The locking thumb control 107 need not have 360 symmetry, so long as it engages the threaded portion of the piston 84, has formations by the user can rotate the control, and presents a contact surface by which to exert a distally directed normal force on the control 106 while receiving a proximally-directed normal force from the control 106 so that the controls 106 and 107 can be in a mutual friction-inducing locking engagement with each other. For example, the locking thumb control 107 can be configured with a winged configuration as illustrated in FIGS. 2f and 2g, with contact surface 113 and arms 119 to facilitate rotation of the control 107 without a tool. The locking thumb control 107 can also be replaced by any other mechanism that can releasably lock the position of the control 106.

In another preferred embodiment constructed in accordance with the present invention, two or more puller wires (not shown) are provided to enhance the ability to manipulate the tip section. In such an embodiment, a second puller wire and a surrounding second compression coil extend through the catheter body and into separate off-axis lumens in the tip section. The lumens of the tip section receiving the puller wires may be in adjacent quadrants. The first puller wire is preferably anchored proximal to the anchor location of the second puller wire. The second puller wire may be anchored to the tip electrode or may be anchored to the wall of the tip section adjacent the distal end of tip section.

The distance between the distal end of the compression coils and the anchor sites of each puller wire in the tip section determines the curvature of the tip section 14 in the direction of the puller wires. For example, an arrangement wherein the two puller wires are anchored at different distances from the distal ends of the compression coils allows a long reach curve in a first plane and a short reach curve in a plane 90.degree. from the first, i.e., a first curve in one plane generally along the axis of the tip section before it is deflected and a second curve distal to the first curve in a plane transverse, and preferably normal to the first plane. The high torque characteristic of the catheter tip section 14 reduces the tendency for the deflection in one direction to deform the deflection in the other direction. Suitable deflection control handles for use with such a catheter are described in U.S. patent application Ser. No. 08/924,611, filed Sep. 5, 1997, entitled "Omni-Directional Steerable Catheter", Ser. No. 09/130,359, filed Aug. 7, 1998, entitled "Bi-Directional Control Handle for Steerable Catheter", and Ser. No. 09/143,426, filed Aug. 28, 1998, entitled "Bidirectional Steerable Catheter with Bidirectional Control Handle", the disclosures of which are hereby incorporated by reference.

As an alternative to the above described embodiment, the puller wires (not shown) may extend into diametrically opposed off-axis lumens in the tip section. In such an embodiment, each of the puller wires may be anchored at the same location along the length of the tip section, in which case the curvatures of the tip section in opposing directions are the same and the tip section can be made to deflect in either direction without rotation of the catheter body. The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. It is understood that the needle control handle can be adapted to extend and retract other components. Moreover, such other components need not extend the length of the catheter body to the tip section.

Accordingly, the foregoing description should not be read as pertaining only to the precise structures described and illustrated in the accompanying drawings, but rather should be read consistent with and as support to the following claims which are to have their fullest and fair scope.

What is claimed is:

1. An injection catheter comprising:
a catheter body;
a tip section distal of the catheter body;
a needle control handle proximal the catheter body, the needle control handle comprising:
an outer body having a piston chamber therein;
a piston having two ends, wherein one end of the piston is slidably mounted within the piston chamber; and
an injection needle extending through the tip section, catheter body, and needle control handle, whereby longitudinal force applied to one of the outer body and the piston causes longitudinal movement of the injection needle to extend past the distal end of the tip section;
wherein at least a portion of the piston has a threaded outer surface, and wherein the needle control handle further comprises:
a thumb control rotatably mounted on the piston and having a threaded inner surface that interacts with the threaded outer surface of the piston; whereby rotation of the thumb control about the piston moves the position of the thumb control relative to the piston, and further whereby the position of the thumb control limits the longitudinal movement of the piston relative to the outer body, and
a locking control rotatably mounted on the piston and having a threaded inner surface that interacts with the threaded outer surface of the piston, whereby rotation of the locking control about the piston moves the locking control toward the thumb control for friction-inducing contact with the thumb control to releasably lock the thumb control in a predetermined position on the piston.

2. An injection catheter of claim 1, wherein the locking control is proximal of the thumb control on the piston.

3. An injection catheter of claim 1, wherein the locking control and thumb control have a generally similar size and configuration.

4. An injection catheter of claim 3, wherein the locking control and thumb control are oriented to oppose each other on the piston.

5. An injection catheter of claim 1, wherein the piston further comprises: a slot extending longitudinally along a portion of its length; and a securing means extending through at least a portion of the outer body and into the slot; whereby, during operation, the securing means limits the distance the piston can be slid proximally out of the piston chamber.

6. An injection catheter of claim 1, further comprising a deflection control handle.

7. An injection catheter of claim 1, wherein the injection needle is attached to the piston by a Luer connector.

8. An injection catheter of claim 1, wherein the needle control handle further comprises a compression spring in the piston chamber between the outer body and the piston; whereby distal force applied to the piston causes distal movement of the piston relative to the outer body, compressing the compression spring, resulting in distal movement of the injection needle relative to the outer body; and whereby absence of the distal force allows the compression spring to decompress, resulting in proximal movement of the injection needle relative to the outer body.

9. A catheter comprising:
a catheter body;
a tip section distal of the catheter body;
a needle control handle comprising:
an outer body having a piston chamber therein;
a piston having two ends, wherein one end of the piston is slidably mounted within the piston chamber; and
an injection needle extending through the tip section, catheter body, and needle control handle, whereby longitudinal force applied to one of the outer body and the piston causes longitudinal movement of the injection needle to extend past the distal end of the tip section;
wherein the needle control handle further comprises:
first and second controls mounted on the piston and are independently and rotationally movable on the piston, wherein a position of the first control limits the longitudinal movement of the piston relative to the outer body, and the first and second controls have friction-inducing surfaces to provide a mutually releasable locking engagement that locks the first control in a predetermined position on the piston.

10. A catheter of claim 9, wherein the friction-inducing surfaces of the first and second controls are adapted to receive a normal force to releasably lock the controls from further rotation on the piston.

11. A catheter of claim 9, wherein the first and second controls are adapted to be rotated in opposing directions to lock with and be released from each other.

12. A catheter comprising:
a catheter body;
a tip section distal of the catheter body;
an extension control handle proximal the catheter body, the control handle comprising:
an outer body having a piston chamber therein; and a piston having two ends, wherein one end of the piston is slidably mounted within the piston chamber; and a component extending through the tip section, catheter body, and control handle, whereby longitudinal force applied to one of the outer body and the piston causes longitudinal movement of the component relative to at least the catheter body;

wherein at least a portion of the piston has a threaded outer surface, and wherein the extension control handle further comprises:

a thumb control rotatably mounted on the piston and having a threaded inner surface that interacts with the threaded outer surface of the piston; whereby rotation of the thumb control about the piston moves the position of the thumb control relative to the piston, and further whereby the position of the thumb control limits the longitudinal movement of the piston relative to the outer body, and a locking control rotatably mounted on the piston and having a threaded inner surface that interacts with the threaded outer surface of the piston, wherein the locking control provides a contact surface adapted to exert a normal force on the thumb control to releasably lock the latter thumb control in a predetermined position on the piston.

13. An injection needle control handle comprising:

an outer body having a piston chamber therein;

a piston having two ends, one end being slidably mounted within the piston chamber, the piston having a portion with a threaded outer surface;

an injection needle, whereby longitudinal force applied to one of the outer body and the piston causes longitudinal movement of the injection needle;

a thumb control rotatably mounted on the piston and having a threaded inner surface that interacts with the threaded outer surface of the piston; whereby rotation of the thumb control about the piston moves a position of the thumb control relative to the piston, and further whereby the position of the thumb control limits the longitudinal movement of the piston relative to the outer body; and a locking control rotatably mounted on the piston and having a threaded inner surface that interacts with the threaded outer surface of the piston, whereby rotation of the locking control about the piston moves the locking control toward the thumb control for friction-inducing contact with the thumb control to releasably lock the thumb control in a predetermined position on the piston.

14. A needle injection control handle of claim 13, wherein each of the locking control and the thumb control has a circular cross section.

15. An extension control handle comprising:

an elongated component;

an outer body having a piston chamber therein;

a piston having an end in the piston chamber and being adapted for longitudinal movement relative to the outer body;

a first control movably mounted on the piston, wherein the first control is rotationally moveable on the piston, and a position of the first control on the piston limits the longitudinal movement of the piston and the elongated component relative to the outer body; and a second control movably mounted on the piston, wherein the second control is rotationally movable on the piston independently of the first control, and is adapted to releasably lock with the first control in a predetermined position on the piston;

whereby longitudinal force applied to at least one of the first and second controls in releasable locking engagement with the other of the first and second controls causes longitudinal movement of the piston and the elongated component relative to the outer body.

16. A control handle of claim 15, wherein the second control is proximal of the first control and the longitudinal force is applied to the second control.

17. A control handle of claim 16, wherein the elongated component is an injection needle.

* * * * *

UNITED STATES PATENT AND TRADEMARK OFFICE
CERTIFICATE OF CORRECTION

| | |
|---|---|
| PATENT NO. | : 8,192,399 B2 |
| APPLICATION NO. | : 12/125890 |
| DATED | : June 5, 2012 |
| INVENTOR(S) | : Christopher J. Birchard |

It is certified that error appears in the above-identified patent and that said Letters Patent is hereby corrected as shown below:

In the Claims

Column 13, Claim 12, line 24.        Delete "latter"

Signed and Sealed this
Thirteenth Day of November, 2012

David J. Kappos
*Director of the United States Patent and Trademark Office*